United States Patent
Ellis

(10) Patent No.: US 7,763,032 B2
(45) Date of Patent: Jul. 27, 2010

(54) METHOD AND APPARATUS FOR FORMING AN APERTURE IN A LENS CAPSULE OF AN EYE

(76) Inventor: Forrest J. Ellis, 35 Lochspur La., Moreland Hills, OH (US) 44022

( * ) Notice: Subject to any disclaimer, the term of this patent is extended or adjusted under 35 U.S.C. 154(b) by 732 days.

(21) Appl. No.: 11/640,621

(22) Filed: Dec. 18, 2006

(65) Prior Publication Data

US 2007/0191862 A1 Aug. 16, 2007

Related U.S. Application Data

(60) Provisional application No. 60/752,075, filed on Dec. 20, 2005.

(51) Int. Cl.
*A61F 9/00* (2006.01)
(52) U.S. Cl. .................................................. 606/107
(58) Field of Classification Search .................. 606/107
See application file for complete search history.

(56) References Cited

U.S. PATENT DOCUMENTS

| | | | |
|---|---|---|---|
| 5,135,530 A | 8/1992 | Lehmer | |
| 5,728,117 A * | 3/1998 | Lash | 606/166 |
| 5,792,166 A | 8/1998 | Gordon et al. | |
| 6,379,370 B1 | 4/2002 | Feinsod | |
| 6,629,980 B1 | 10/2003 | Eibschitz-Tsimhoni | |
| 2004/0260254 A1* | 12/2004 | Neilson et al. | 604/297 |

FOREIGN PATENT DOCUMENTS

GB 2247174 A * 2/1992

* cited by examiner

*Primary Examiner*—Todd E Manahan
*Assistant Examiner*—Kevin Everage
(74) *Attorney, Agent, or Firm*—Tarolli, Sundheim, Covell & Tummino LLP

(57) ABSTRACT

An improved cutter assembly is used to form an aperture in a lens capsule of an eye. The cutter assembly is resiliently deflectable between a contracted condition and an expanded condition. When the cutter assembly is in the contracted condition, it is moved through an opening in the eye into alignment with an anterior portion of lens capsule of the eye. The cutter assembly is then operated to the expanded condition and moved against the anterior portion of the lens capsule under the influence of fluid pressure. To move the cutter assembly against the anterior portion of the lens capsule, a seal engages an anterior portion of the lens capsule and a conduit connected with the cutter assembly is connected in fluid communication with a source of low pressure (vacuum).

9 Claims, 3 Drawing Sheets

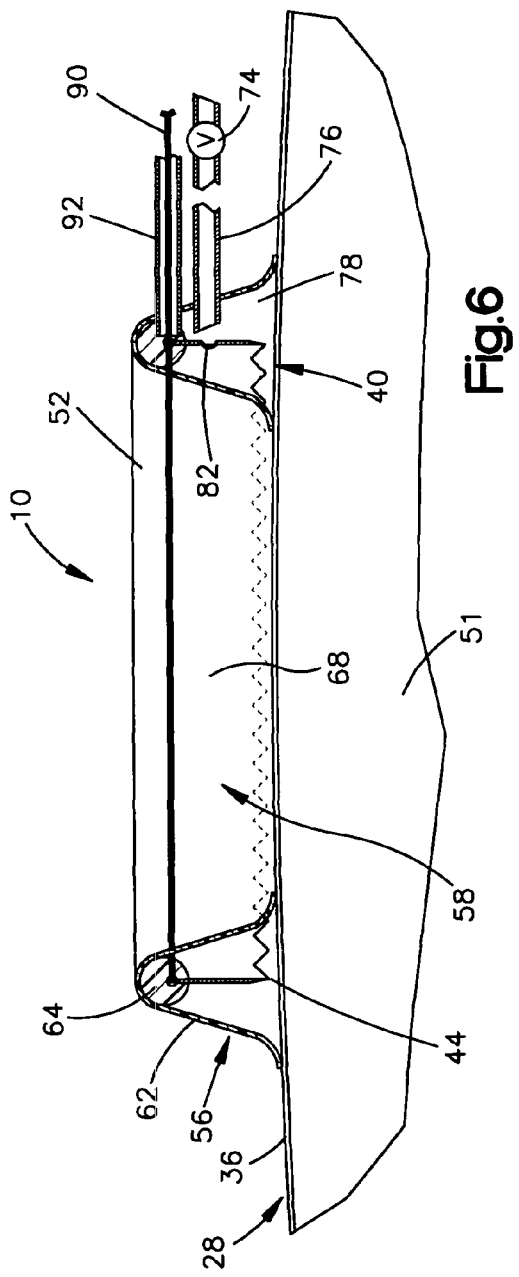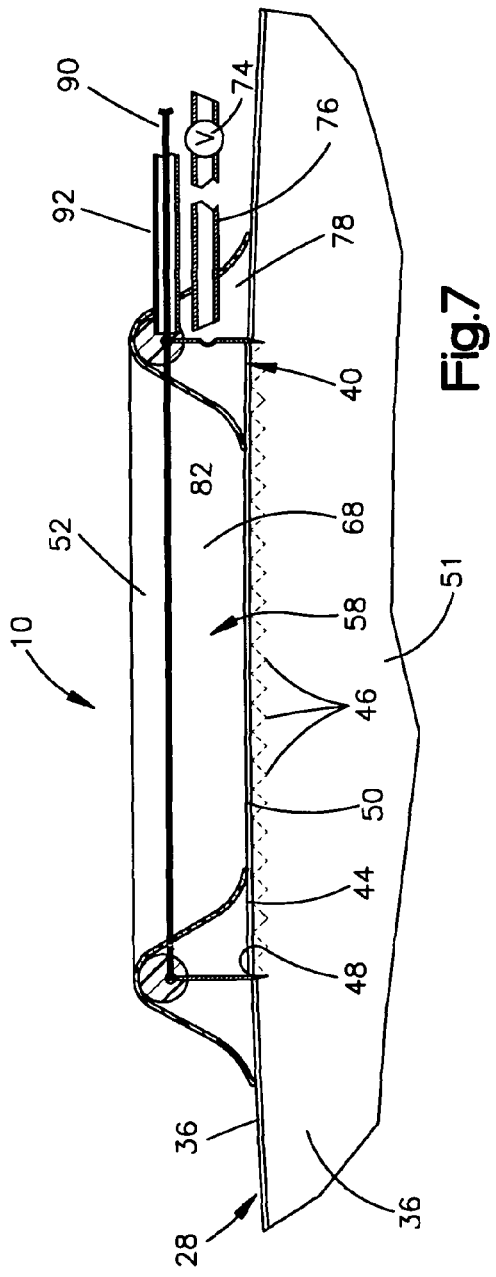

METHOD AND APPARATUS FOR FORMING AN APERTURE IN A LENS CAPSULE OF AN EYE

RELATED APPLICATION

This application claims priority from U.S. Provisional Application No. 60/752,075, filed Dec. 20, 2005, the subject matter of which is incorporated herein by reference.

BACKGROUND OF THE INVENTION

The present invention relates to a new and improved method and apparatus for use in the field of cataract surgery. More specifically, the present invention relates to a new and improved method and apparatus of forming an aperture in the anterior portion of the lens capsule of an eye.

A cataract impairs vision by clouding the lens of an eye. In a normal eye, the lens is clear and helps to focus an image on the retina of the eye. The lens must be clear for the retina to receive a sharp image. If the lens is cloudy from a cataract, the image received by the retina is blurred.

To eliminate a cataract with a known surgical procedure, a small incision is made in the cornea or sclera of the eye. A surgical instrument is inserted through the incision in the cornea and is used to form an incision in the anterior capsule of the lens of the eye. After this instrument has been removed from the eye, a forceps or other instrument is inserted through the incision into the anterior chamber. Forceps or a cystotome or bent small gauge needle is used to capture a portion of the lens capsule adjacent to the incision. These instruments are then moved to tear the lens capsule and form an aperture in the lens capsule.

A small probe is inserted through the incision in the cornea and the aperture in the lens capsule. The probe emits ultrasound waves which soften and break up the nucleus of the lens so that it can be removed by suction. The process may be referred to as phacoemulsification. After the natural lens has been removed, it may be replaced by an artificial lens.

Difficulty is sometimes encountered in tearing the lens capsule to form an aperture in the anterior portion of the lens capsule. The lens capsule is then manipulated with instruments and torn to form the aperture. The tearing motion can result in the formation of a tear having an undesirable configuration. Various methods and devices for use in forming an aperture in the anterior portion of a lens in an eye are disclosed in U.S. Pat. Nos. 5,135,530; 5,728,117; 5,792,166; 6,379,370; and 6,629,980.

SUMMARY OF THE INVENTION

The present invention relates to a new and improved method and apparatus for forming an aperture in a lens capsule of an eye. The apparatus includes a cutter assembly which is insertable through an opening in the eye. The cutter assembly is moved against the anterior portion of the lens capsule under the influence of fluid pressure. As the cutter assembly is moved against the anterior portion of the lens capsule under the influence of fluid pressure, the lens capsule is cut to form an aperture in the lens capsule.

The cutter assembly may be moved against the anterior portion of the lens capsule by establishing a pressure differential across the cutter assembly. This pressure differential may be established by evacuating a space disposed between the cutter assembly and the anterior portion of the lens capsule. One or more seal members may be provided in the cutter assembly to sealingly engage the anterior portion of the lens capsule.

BRIEF DESCRIPTION OF THE DRAWINGS

The foregoing and other features of the invention will become more apparent upon consideration of the following description taken in connection with the accompanying drawings wherein:

FIG. 6 is a schematic illustration of the manner in which the cutter assembly engages the lens capsule when the cutter assembly is in the extended condition; and FIG. 7 is a schematic illustration of the manner in which a cutter member in the cutter assembly cuts the lens capsule.

DESCRIPTION OF SPECIFIC PREFERRED EMBODIMENTS OF THE INVENTION

Figure 1:
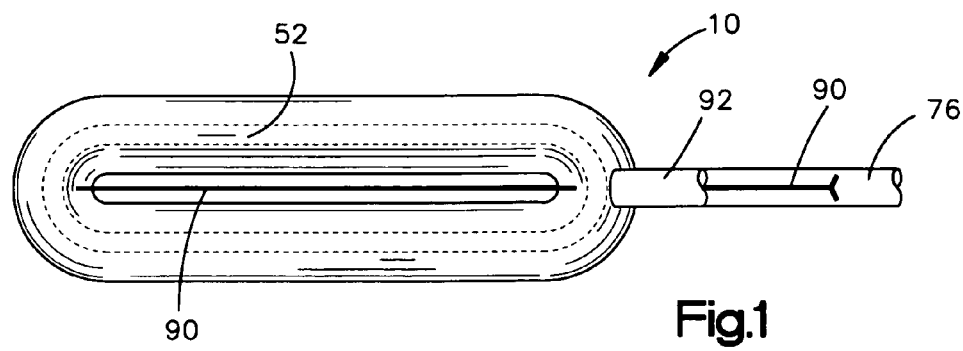
FIG. 1 is an enlarged schematic top plan view of a cutter assembly constructed in accordance with the present invention and illustrated in a contracted condition for insertion through a small opening in the peripheral portion of the cornea or sclera of the eye.

During cataract surgery, a cutter assembly 10 (FIGS. 1-7) is utilized to form an aperture in a lens capsule of an eye. To enable the cutter assembly 10 to be inserted through a relatively small incision or opening 12 in a peripheral portion of the cornea 14 or in the sclera of the eye, the cutter assembly is operable to a contracted condition illustrated in FIG. 1. When the cutter assembly 10 is in the contracted condition of FIG. 1, the cutter assembly has a generally oval configuration. The oval configuration of the cutter assembly 10 results in the cutter assembly having an elongated configuration so that it can be inserted through a small incision 12 in (FIG. 4) in a cornea 14 or sclera of an eye 16.

When the contracted cutter assembly 10 is to be inserted into the eye 16, the opening or incision 12 is formed in the eye. While the cutter assembly 10 is in the contracted condition of FIG. 1, the cutter assembly is moved through the opening or incision 12 (FIG. 4) into the anterior chamber 20 of the eye. The contracted cutter assembly is moved into alignment with an anterior portion 24 of a lens 28 in the eye 16. At this time, the cutter assembly 10 is also aligned with the central opening in the iris 32 of the eye 16.

Figure 2:
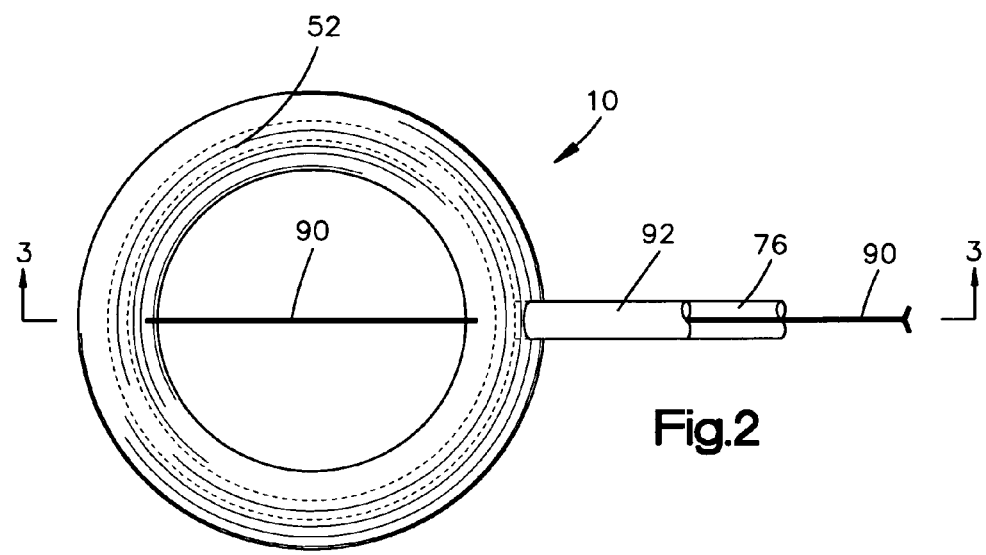
FIG. 2 is a schematic top plan view, generally similar to FIG. 1, of the cutter assembly in an extended condition in which it is utilize to cut the anterior portion of a lens capsule.
Figure 3:
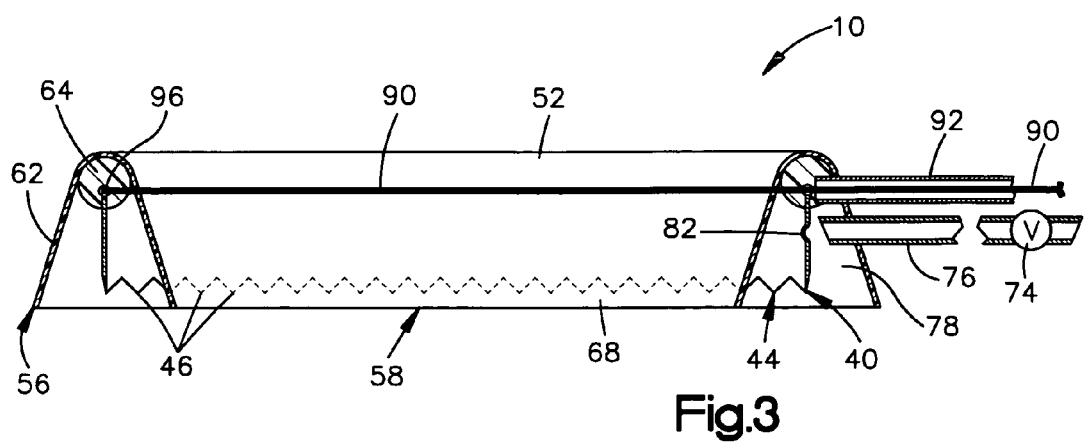
FIG. 3 is an enlarged schematic sectional view, taken generally along the line 3-3 of FIG. 2, further illustrating the construction of the cutter assembly.
Figure 4:
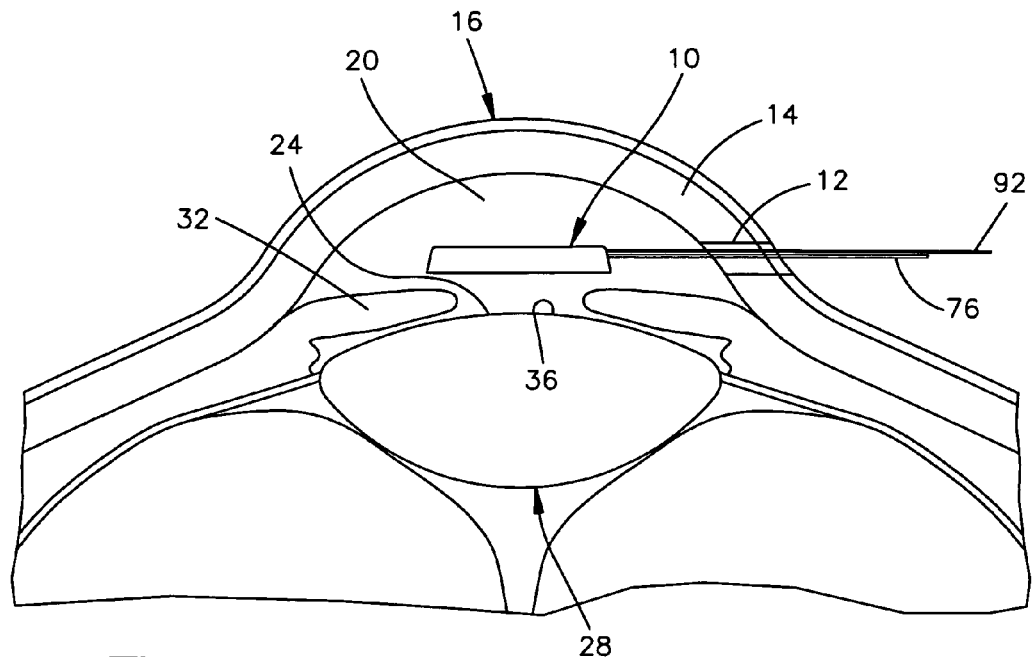
FIG. 4 is a schematic illustration depicting the manner in which the cutter assembly is moved through an opening in the peripheral cornea or sclera into alignment with an anterior portion of a lens capsule of an eye, the cutter assembly being illustrated in the contracted condition of FIG. 1.

Once the cutter assembly 10 has moved into the alignment with the central opening in the iris of the eye 16, the cutter assembly is operated from the contracted condition of FIGS. 1 and 4 to the extended condition of FIGS. 2, 3, and 5-7. When the cutter assembly 10 is in the extended condition it has a circular configuration, as viewed in FIG. 2. Although the extended cutter assembly 10 has been illustrated in FIG. 2 as having a circular configuration, it is contemplated that the cutter assembly may have a different configuration. For example, the extended cutter assembly 10 may have an oval configuration.

The extended cutter assembly 10 is moved downward (as viewed in FIG. 5) through the central opening in the iris 32 into engagement with the anterior portion of the capsule 36 of the lens 28. Once the cutter assembly 10 has moved into engagement with the capsule 36 of the lens 28 (FIG. 6), the cutter assembly 10 is moved against the anterior portion 24 of the lens capsule 36 to form an aperture or opening in the lens 28 (FIG. 7).

Figure 5:
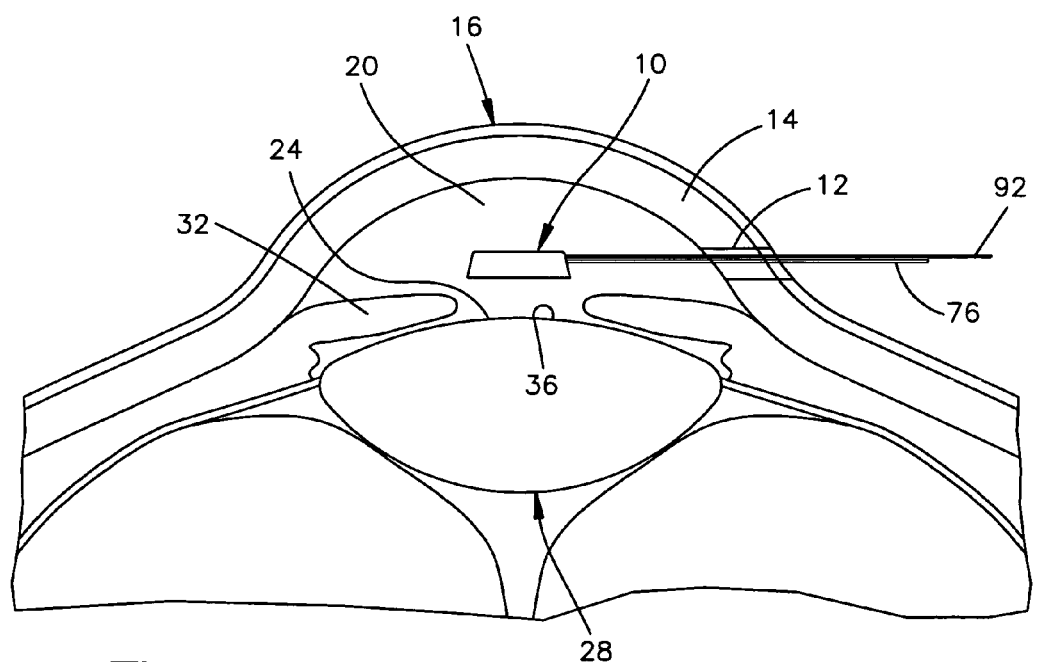
FIG. 5 is a schematic illustration, generally similar to FIG. 4, illustrating the relationship of the cutter assembly to the anterior portion of the lens capsule when the cutter assembly is in the extended condition of FIGS. 2 and 3.

To form the aperture or opening in the lens 28, the cutter assembly 10 includes a cutter member 40 (FIG. 3) which is resiliently deflectable between an oval configuration when the cutter assembly is in the contracted condition of FIG. 1 and a more circular configuration when the cutter assembly 10 is in the extended condition of FIGS. 2 and 3. The cutter member 40 has a circular cutting edge 44 (FIG. 3) which forms a circular incision in the capsule 36 at the anterior portion 24 of the lens 28 (FIG. 5). The cutting edge 44 (FIG. 3) may have an irregular configuration to provide a circular series of peaks or sharp points 46 along the cutting edge on the cutter member 40. However, if desired, the peaks or sharp points 46 may be eliminated and the cutter member may be formed with a continuous knife edge having a smooth circular configuration. Alternatively, the cutter member may have one or more sharp teeth to initiate the cut.

The cutter assembly 10 is pressed against the anterior portion 24 of the lens 28 under the influence of fluid pressure. The fluid pressure provides a force which moves the cutting edge 44 of the cutter member 40 against the lens capsule 36. The cutting edge 44 forms a circular incision 48 (FIG. 7) in the lens capsule 36 as the cutting edge is pressed against the lens capsule by fluid pressure. However, if the cutting edge 44 of the cutter member 40 has a noncircular configuration, a noncircular incision 48 would be formed.

Once the incision 48 has been formed in the anterior portion of the lens capsule 36, the pressing of the cutter assembly 10 against the lens capsule 36 under the influence of pressure is interrupted. The cutter assembly 10 is then moved upward away from the lens capsule 36. Once the cutter assembly 10 has been disengaged from the lens capsule 36, the cutter assembly is operated from the expanded condition of FIGS. 2, 3 and 5-7 back to the contracted condition of FIGS. 1 and 4. The contracted cutter assembly 10 is then withdrawn from the anterior chamber 20 of the eye 16 by moving the cutter assembly back through the incision 12 (FIG. 4) in the cornea 14.

Forceps and/or other suitable instrument is then moved through the incision 12. A piece 50 (FIG. 7) cut from the remainder of the lens capsule 36 by the cutter assembly 10 is gripped by the instrument. The piece 50 of the lens capsule is disengaged from the lens 28. The instrument is then used to move the circular piece 50 of the lens capsule out of the anterior chamber 20 of the eye 16 through the incision 12. The piece 50 may have a circular or noncircular configuration. Thereafter, the probe of a phacoemulsification apparatus is moved through the incision 12 into the anterior chamber 20 of the eye.

The probe of the phacoemulsification apparatus is moved through the aperture or opening 48 formed in the lens capsule 36 and into the nucleus 51 (FIG. 7) of the lens 28. As this occurs, the probe emits ultrasound waves which soften and break up the nucleus 51 of the lens 28 so that it can be removed from the capsule 36 by suction. After the nucleus 51 of the lens 28 have been removed, it may be replaced by an artificial lens. The artificial lens is held in place by the remaining portion of the lens capsule 36. The foregoing description has been in conjunction with cataract surgery which includes phacoemulsification. However, other surgical procedures may be utilized if desired.

To form the aperture 48 in the anterior portion of the lens capsule 36, the cutter assembly 10 is pressed against the lens capsule under the influence of fluid pressure. Although a fluid pressure force may be applied to the cutter assembly 10 in different ways, the fluid pressure force is applied to the cutter assembly by establishing a pressure differential across the cutter assembly.

To enable the pressure differential to be established, the cutter assembly 10 sealingly engages the lens capsule 36. A space is formed between the cutter assembly 10 and the lens capsule 36. This space is then evacuated. Evacuation of a space between the cutter assembly 10 and the lens capsule 36 results in a fluid pressure differential which is effective to move the cutter assembly 10 relative to the lens capsule 36.

Once the fluid pressure in space between the cutter assembly 10 and lens capsule 36 has been reduced, the relatively high fluid pressure against an outer side 52 of the cutter assembly 10 presses the cutting edge 44 of the cutter member 40 against the surface of the lens capsule 36. The cutter member 40 is pressed against the lens capsule 36 with sufficient force to enable the cutter member to form the incision 48 in the lens capsule 36. To provide for a sealing engagement of the cutter assembly 10 with the lens capsule 36, one or more seal members may be provided.

In the embodiment of the cutter assembly 10 illustrated in FIG. 3, the cutter assembly is provided with two seal members, that is, a radially outer seal member 56 and a radially inner seal member 58. The radially outer seal member 56 is formed by a resilient flap 62 which extends axially downward (as viewed in FIG. 3) and radially flares outward from a base 64 of the cutter assembly 10. Similarly, the inner seal member 58 includes a resilient flap 68. The flap 68 extends axially downward and flares radially inward from the base 64.

The flexible flaps 62 and 68 extend axially downward (as viewed in FIG. 3) past the cutting edge 44 on the cutter member 40. Therefore, when the cutter assembly 10 has been positioned in alignment with the lens 28 (FIG. 5) and moved downward toward the lens, the two flaps 62 and 68 engage the anterior surface of the lens capsule 36 before the cutting edge 44 on the cutter member 40 engages the lens capsule (FIG. 6). This results in formation of an annular seal between the flap 62 and an annular surface area on the anterior portion of the lens capsule 36. Similarly, an annular seal is formed between the flap 68 and an annular surface area on the anterior portion of the lens capsule 36.

The annular seals formed by engagement of the flaps 62 and 68 with the surface of the lens capsule 36 (FIG. 6) are disposed in a coaxial relationship with each other and with the cylindrical cutter member 40. The annular seal formed by the flap 62 is disposed radially outward of the cutter member 40 while the annular seal formed by the flap 68 is disposed radially inward of the cutter member.

After the flaps 62 and 68 have moved into sealing engagement with the lens capsule 36, a control valve 74 (FIGS. 3, 6, and 7) is operated from a closed condition to an open condition to connect a conduit 76 in fluid communication with a source of low pressure (vacuum). This results in a reduction in the fluid pressure in an annular chamber 78 which is formed between the cutter assembly 10 and the anterior surface of the lens capsule 36. A portion of the chamber 78 is disposed radially outward of the cutter member 40 while another portion of the chamber 78 is disposed radially inward of the cutter member. One or more openings 82 (FIG. 3) are formed in the cutter member 40 to connect the radially inner and outer portions of the annular chamber 78 in fluid communication.

When the pressure in the annular chamber 78 is reduced, fluid pressure against the outer side 52 of the cutter assembly 10 presses the cutter assembly toward the lens capsule 36. This is because the fluid pressure in the anterior chamber 20 (FIG. 5) of the eye 16 will be greater than the fluid pressure in the chamber 78 once the control valve 74 has been opened to connect the conduit 76 in fluid communication with a source of low pressure (vacuum).

The fluid pressure differential between the chamber 78 in the cutter assembly 10 and the ambient fluid pressure in the anterior chamber 20 of the eye 16 is effective to urge the cutter assembly 10 downward (as viewed in FIG. 6) toward the lens capsule 36. At the same time, fluid pressure against an inner side of the lens capsule 36 is effective to urge the lens capsule upward (as viewed in FIG. 6) toward the cutter assembly 10. As this occurs, the flaps 62 and 68 are resiliently deflected. Thereafter, the cutting edge 44 of the cutter member 40 is drawn against the lens capsule 36 with sufficient force to form an incision 48 (FIG. 7) in the lens capsule. Once the incision 48 has been formed in the lens capsule by the cutter member 40, the control valve 74 is operated to vent the chamber 78 to atmosphere.

Operation of the control valve 74 to vent the chamber 78 to atmosphere eliminates the pressure differential between the chamber 78 and the anterior chamber 20 of the eye 16. If desired, the control valve 74 may be constructed so as to direct a fluid pressure which is slightly greater than atmospheric pressure into the chamber 78. The entire system could be attached to commercially available irrigation/aspiration phacoemulsification or other similar devices for cataract surgery for removed of the lens and vitreous material.

Once the chamber 78 has been vented, the resiliently deflected flaps 62 and 68 spring back to the frustro-conical configuration illustrated in FIG. 3. This disengages the cutting edge 44 of the cutter member 40 from the anterior surface portion of the lens 28. The cutter assembly 10 is then operated to the contracted condition of FIG. 1. The contracted cutter assembly 10 is then moved through the incision 12.

Forceps or another suitable instrument is moved through the incision 12. The forceps is moved into the aperture 48 (FIG. 7) formed in the lens capsule 36 by the cutter member 40 in the cutter assembly 10. The forceps are then used to grip the piece 50 of the lens capsule 36 and to move the piece of the lens capsule 36 through the incision 12. The formation of the circular opening in the lens capsule 36 enables the probe of a phacoemulsification or other apparatus to be moved through the incision 12 in the cornea 14 and into the nucleus 51 of the lens 28.

The seal flaps 62 and 68 (FIG. 3) are integrally formed from a single piece of flexible material. The seal flaps 62 and 68 are formed of a flexible polymeric material. However, the seal flaps 62 and 68 may be formed of any other suitable material any may be formed of a plurality of pieces.

The flexible material forming the seal flaps 62 and 68 extends along radially inner and outer sides of the annular base 64 of the cutter assembly 10. The resiliently flexible cutter member 40 is embedded in and secured to the flexible polymeric material of the annular base 64. The cutter member 40 is formed of metal. However, the cutter member may be formed of a different material if desired. For example, the cutter member 40 may be formed of a polymeric material. The flexible low pressure conduit 76 extends through the flap 62 into the chamber 78.

The illustrated embodiment of the cutter assembly 10 has a pair of flaps 62 and 68 which sealingly engage the lens capsule 36 to enable a pressure differential to be established between the inside of the cutter assembly and the exterior of the cutter assembly. The flaps 62 and 68 are formed from one piece of material. However, the flaps 62 and 68 may be formed separately or may be integrally molded as one piece with the base 64. However, if desired, the cutter assembly 10 may utilize seal members which are different from the flaps 62 and 68. For example, a pair of sealing strips may be connected with the base and urged toward the lens capsule 36 by suitable springs. Alternatively, one or more seal strips may be mounted on the cutter member 40.

In the illustrated embodiment of the cutter assembly 10, a pair of annular seals are formed between the cutter assembly and the lens 36 by the flaps 62 and 68. However, only a single seal may be utilized if desired. For example, the flap 68 may be eliminated and a single seal formed by the flap 62. If this is done, a panel may extend across the base 64 to seal upper end of the central opening in the base 64. This would result in the chamber 78 extending across the entire lower side of the cutter assembly 10. Alternatively, the low pressure chamber may be formed entirely radially inward from the cutter member 40 by the flap 68 or other seal member. If this is done, the central opening in the cutter assembly 10 would be closed and the conduit 76 would be extended through or above the cutter member 40 into the resulting chamber. It should be understood that there are many different sealing arrangements which may be utilized to establish a pressure differential across the cutter assembly 10.

As initially formed, the cutter assembly 10 has the contracted configuration illustrated in FIG. 1. The cutter assembly 10 is resiliently deflected from the contracted configuration of FIG. 1 to the expanded configuration of FIG. 2 by tensioning a flexible wire 90 disposed within a conduit 92. Polymeric material of the conduit 92 is flexible. However, the polymeric material of the conduit 92 has sufficient rigidity to enable force to be transmitted from the conduit 92 to the base 64 of the cutter assembly 10 when the wire 90 is tensioned.

In the illustrated embodiment of the invention, the wire 90 is disposed in a conduit 92 which is separate from the low pressure conduit 76. However, if desired, the wire 90 may extend through the low pressure conduit 76. If this is done, the conduit 92 would be eliminated. Of course, the conduit 76 would have sufficient rigidity to transmit force required to oppose force transmitted through the wire 90 when the cutter assembly 10 is in the extended condition of FIGS. 2 and 3. Alternatively, the conduits 76 and 92 may be integrally formed as one piece with two passages, that is, one passage for the wire 90 and a second passage for vacuum.

After the contracted cutter assembly 10 (FIG. 4) has been moved through the incision 12 in the cornea 14 into the anterior chamber 20, the wire 90 (FIG. 3) is tensioned. The left end (as viewed in FIG. 3) of the wire 90 is secured to the resiliently deflectable cutter member 40 at a connection 96. The left (as viewed in FIG. 3) end of the conduit 92 engages a portion of the cutter member 40 which is diametrically opposite from the connection 96. In addition, the conduit 92 engages the base 64 of the cutter assembly 10. When the wire 90 is tensioned and the end of the conduit 92 is pressed against the cutter assembly 40 and base 64, the cutter assembly 10 is resiliently deflected. This results in the cutter assembly 10 being resiliently deflected from the oval configuration of FIG. 1 to the circular configuration of FIGS. 2 and 3.

When the wire 90 is released, the transmission of force through the wire and through the conduit 92 is interrupted. This results in the cutter member 40 and base 64 of the cutter assembly 10 being released. When this happens, the natural resilience of the metal cutter member 40 and base 64 causes them to spring back to the oval configuration illustrated in FIG. 1.

If desired, the cutter assembly 10 may be initially formed with the circular configuration of FIG. 2 and resiliently deflected to the oval configuration of FIG. 1. If this is done, it is believed that a relatively stiff rod or other member will be extended diametrically across the base 64 to a connection with the cutter member 40. The conduit 92 would then be tensioned and the rod pushed to move the cutter assembly from the circular expanded condition of FIG. 2 to the oval contracted condition of FIG. 1. Alternatively, it is contemplated that the cutter member 40 may be formed from a memory metal which, when released, moves to the desired configuration.

It is contemplated that the cutter assembly 10 will be relatively small in size to facilitate moving of the cutter assembly through the corneal incision 12 (FIG. 4) and to facilitate positioning of the cutter assembly in the anterior chamber 20 of the eye 16. It is believed that the cutter assembly 10 may have a cutter member 40 which has a diameter of approximately 4 millimeters when the cutter assembly is in the expanded condition of FIG. 3. It should be understood that the foregoing specific size and shape of the cutter member 40 has been set forth herein for purposes of clarity of description and not for purposes of limiting the invention. It is contemplated that a variety of different diameters and/or shapes may be provided.

In view of the foregoing description, it is apparent that the present invention provides a new and improved method and apparatus for forming an aperture in a lens capsule 36 of an eye 16. The apparatus includes the cutter assembly 10 which is insertable through an opening 12 in eye 16. The cutter assembly 10 is moved relative to the anterior portion of the lens capsule 36 under the influence of fluid pressure. As the cutter assembly 10 is moved relative to the anterior portion of the lens capsule 36 under the influence of fluid pressure, the lens capsule is cut to form the aperture in the lens capsule.

The cutter assembly 10 may be moved relative to the anterior portion of the lens capsule 36 by establishing a pressure differential across the cutter assembly. This pressure differential may be established by evacuating a space 78 disposed between the cutter assembly 10 and the anterior portion of the lens capsule 36. One or more seal members 56 and/or 58 may be provided in the cutter assembly 10 to sealingly engage the anterior portion of the lens capsule 36.

Having described the invention, the following is claimed:

1. A method of forming an aperture in a lens capsule of an eye, said method comprising the steps of:
    forming an opening in the eye,
    moving a cutter assembly through the opening in the eye into an anterior chamber of the eye and into alignment with an anterior portion of the lens capsule of the eye,
    engaging the lens capsule of the eye with seal members in the cutter assembly to form a cutter chamber in which a cutter in the cutter assembly is disposed,
    evacuating the cutter chamber,
    moving the cutter in the evacuated cutter chamber under the influence of fluid pressure contained in the anterior chamber of the eye and applied against an outer side of the cutter assembly, and
    cutting the anterior portion of the lens capsule with the cutter as the cutter is moved in the evacuated cutter chamber under the influence of fluid pressure contained in the anterior chamber of the eye and applied against the outer side of the cutter assembly.

2. A method as set forth in claim 1 wherein said step of moving the cutter assembly through the opening in the eye is performed while the cutter assembly has a first configuration, and, after the cutter assembly has moved through the opening in eye and while the cutter is completely disposed in the anterior chamber of the eye, changing the configuration of the cutter assembly to a second configuration which is different than the first configuration.

3. A method as set forth in claim 1 further wherein said step of engaging the lens capsule of the eye with seal members includes engaging the anterior portion of the lens capsule with an inner side of a first flap disposed adjacent to a first side of said cutter, and engaging the anterior portion of the lens capsule with an inner side of a second flap disposed adjacent to a second side of said cutter, said step of moving the cutter being performed while outer sides of the first and second flaps are exposed to the fluid pressure contained in the anterior chamber of the eye and while the inner sides of the first and second flaps are pressed against the anterior portion of the lens capsule by the fluid pressure applied against the outer sides of the first and second flaps, said step of cutting the anterior portion of the lens capsule includes cutting the anterior portion of the lens capsule at a location disposed between locations where the inner sides of the first and second flaps engage the anterior portion of the lens capsule.

4. A method as set forth in claim 3 wherein said step of engaging the anterior portion of the lens capsule with the inner side of the first flap includes engaging a first annular area on the anterior portion of the lens capsule with the inner side of the first flap, said step of engaging the anterior portion of the lens capsule with the inner side of the second flap includes engaging a second annular area on the anterior portion of the lens capsule with the inner side of the second flap, said step of cutting the anterior portion of the lens capsule with the cutter includes forming an annular incision in the lens capsule at a location between the first and second annular areas on the lens capsule.

5. A method as set forth in claim 1 wherein said step of evacuating the cutter chamber includes conducting fluid flow through an opening formed in the cutter.

6. A method as set forth in claim 1 wherein said step of moving a cutter assembly through an opening in the eye into the anterior chamber of the eye is performed while the cutter assembly has a noncircular configuration, said method further includes tensioning an elongated member connected with the cutter to change the configuration of the cutter assembly from a noncircular configuration to a circular configuration while the cutter assembly is disposed in the anterior chamber of the eye.

7. An apparatus for use in forming an aperture in a lens capsule of an eye, said apparatus comprising a cutter assembly having a circular base, a circular cutter connected with said base, a first flap connected with said base and extending radially and axially from said base along a first side of said cutter, said first flap having an inner side surface which is engagable with the anterior portion of the lens capsule and an outer side surface which is exposed to fluid pressure contained in the anterior chamber of the eye, said inner and outer side surfaces of said first flap being disposed on opposite sides of said first flap, a second flap connected with said base and extending radially and axially from said base along a second side of said cutter, said second flap having an inner side surface which is engagable with the anterior portion of the lens capsule and an outer side surface which is exposed to fluid pressure contained in the anterior chamber of the eye, said inner and outer side surfaces of said second flap being disposed on opposite sides of said second flap, said first and second flaps cooperating with the anterior portion of the lens capsule to at least partially define a cutter chamber in which said cutter is at least partially disposed when said inner side surfaces of said first and second flaps are disposed in engagement with the anterior portion of the lens capsule, and a conduit which is connected in fluid communication the cutter chamber and which conducts fluid from the cutter chamber toward a source of low pressure to reduce the fluid pressure in the cutter chamber to a fluid pressure which is less than the fluid pressure contained in the anterior chamber of the eye, said cutter being movable under the influence of fluid pressure contained in the anterior chamber of the eye and applied against an outer side of the cutter assembly to cut the anterior portion of the lens capsule at a location between the first and second flaps when said inner side surfaces of said first and second flaps are disposed in engagement with the anterior portion of the lens capsule.

8. An apparatus as set forth in claim 7 wherein said cutter has an opening through which fluid pressure is transmitted between a portion of the cutter chamber disposed on a first side of said cutter and a portion of said cutter chamber disposed on a second side of said cutter.

9. An apparatus as set forth in claim 7 wherein said cutter assembly further includes a force transmitting member which is connected with said base and transmits force to change the configuration of said cutter assembly between an oval configuration which facilitates movement of said cutter assembly through an opening in a cornea of the eye and a circular configuration which facilitates cutting of a circular opening in the lens capsule of the eye.

* * * * *